United States Patent [19]

Butte, Jr. et al.

[11] 4,235,821
[45] Nov. 25, 1980

[54] HYDROGENATION OF ALIPHATIC NITRILES TO PRIMARY AMINES

[75] Inventors: Walter A. Butte, Jr., West Chester; William J. Murtaugh, Eddystone; Richard E. Mitchell, Glenmills, all of Pa.

[73] Assignee: Suntech, Inc., Philadelphia, Pa.

[21] Appl. No.: 8,315

[22] Filed: Feb. 1, 1979

[51] Int. Cl.$^2$ .................... C07C 87/14; C07C 85/12
[52] U.S. Cl. .................... 564/491; 564/493; 564/505; 564/511; 564/512
[58] Field of Search .................... 260/583 K

[56] References Cited

U.S. PATENT DOCUMENTS

| | | | |
|---|---|---|---|
| 3,372,195 | 3/1968 | Little | 260/563 D X |
| 3,880,928 | 4/1975 | Drake | 260/583 K X |
| 3,896,173 | 7/1975 | Drake | 260/583 K X |
| 3,896,174 | 7/1975 | Drake | 260/583 K X |
| 3,898,286 | 8/1975 | Drake | 260/583 K X |
| 3,962,337 | 6/1976 | Drake | 260/583 K |

*Primary Examiner*—Paul F. Shaver
*Attorney, Agent, or Firm*—J. Edward Hess; Donald R. Johnson; Paul Lipsitz

[57] ABSTRACT

In the process of hydrogenating aliphatic nitriles to primary amines whereby the nitrile is hydrogenated in a solvent system containing added ammonia using a cobalt or ruthenium catalyst, the improvement of employing an ether as solvent and carrying out the hydrogenation in the presence of water in an amount of from about 5% to about 15% by volume of the ether solvent whereby the rate of reaction is increased, and selectivity to primary amine products is increased.

10 Claims, 2 Drawing Figures

HYDROGENATION OF ALIPHATIC NITRILES TO PRIMARY AMINES

CROSS REFERENCE TO RELATED APPLICATIONS

This application is related to the following applications filed of even date herewith: Walter A. Butte, Jr. and Howard P. Angstadt, entitled "Hydrogenation of Aromatic Amines", Ser. No. 8,309; Walter A. Butte, Jr., William J. Murtaugh and Howard P. Angstadt, entitled "Process for Hydrogenating Aromatic Dinitriles", Ser. No. 8,313; Walter A. Butte, Jr. and William J. Murtaugh, entitled "Hydrogenation of Aromatic Nitriles to Primary Amines", Ser. No. 8,310.

It is known in the art to effect hydrogenation of aliphatic and aromatic nitriles to the corresponding amines in the presence of various catalytic materials. For example, U.S. Pat. No. 3,069,469 discloses the hydrogenation of aromatic nitriles with a combined cobalt and nickel catalyst where the nitrile, hydrogen, ammonia, and solvent (such as the isomeric xylenes, dioxane, and aliphatic alcohols) are brought into contact with the catalyst. A combined cobalt-nickel catalyst is employed in order to reduce the amount of undesirable secondary amines which contaminate the desired primary amine products and this phenomenon is common in nitrile hydrogenation.

In U.S. Pat. No. 3,331,877 a process is disclosed for preparing 1,3-diaminopropane by heating an alkylene bis-oxydipropionitrile with a hydrogenation catalyst (e.g. nickel or cobalt) in the presence of ammonia and with or without a solvent such as methanol, ethanol, tetrahydrofuran and dioxane.

Another disclosure of interest is U.S. Pat. No. 3,252,248 which details the catalytic hydrogenation or organic nitrogen-containing carbon compounds (including aliphatic and aromatic nitriles) to amines in a liquid phase system using a specifically prepared sintered catalyst of cobalt or nickel. Because such specially prepared catalysts are said to be of high mechanical strength they are suitable when used in a method in which the initial material, either alone or in admixture with a solvent such as water, tetrahydrofuran, ammonia, methanol or the reaction product formed, is trickled together with hydrogen over the catalyst in a reaction tube. In Example 1 of the patent, an aliphatic nitrile (aminoacetonitrile) is hydrogenated in a mixture of liquid ammonia and an aqueous aminonitrile solution (about 6.6% of the total liquid reactants being water) in the presence of the specially prepared sintered catalyst to obtain ethylenediamine.

Also of interest is the publication of H. Rupe and E. Hodel in Hel. Chem. Acta 6 865–880 (1923) which points out that in the hydrogenation of nitriles with a nickel catalyst in an aqueous system at atmospheric pressure, the water reacts with intermediates to form significant aldehydes which, in turn, leads to secondary amines being present in the reaction product. A later publication (U.S. Pat. No. 3,372,195, 1968) confirms that water is detrimental in reducing nitriles for primary amines. Thus, in U.S. Pat. No. 3,372,195 it is reported that numerous types of nitriles including aliphatic and aromatic nitriles and cyanoethylated glycols may be converted to the corresponding primary amines by hydrogen reduction under pressure with a ruthenium catalyst and in the presence of ammonia using as a solvent system any one of a number of solvents including water. However, the disclosure adds that with nitriles having a molecular weight lower than about 200, water is not preferred due to its tendency to cause increased by-product formation. It has now been found in the hydrogenation to primary amines of aliphatic nitriles, in the presence of ammonia and using a cobalt or ruthenium catalyst, that the presence of a specific amount of water significantly improves the process. A particularly valuable improvement is the high yield of primary amine product obtained at significant reaction rate. Another unexpected advantage is that although by-product secondary amines are present they do not appear to be detrimental to the catalyst and the process of the invention permits long catalyst life.

In accord with the process of the invention an aliphatic nitrile is advantageously hydrogenation to a primary amine in a solvent system comprising an ether, ammonia and an amount of water of from about 5% to about 15% by volume of the solvent used.

Figure 1:
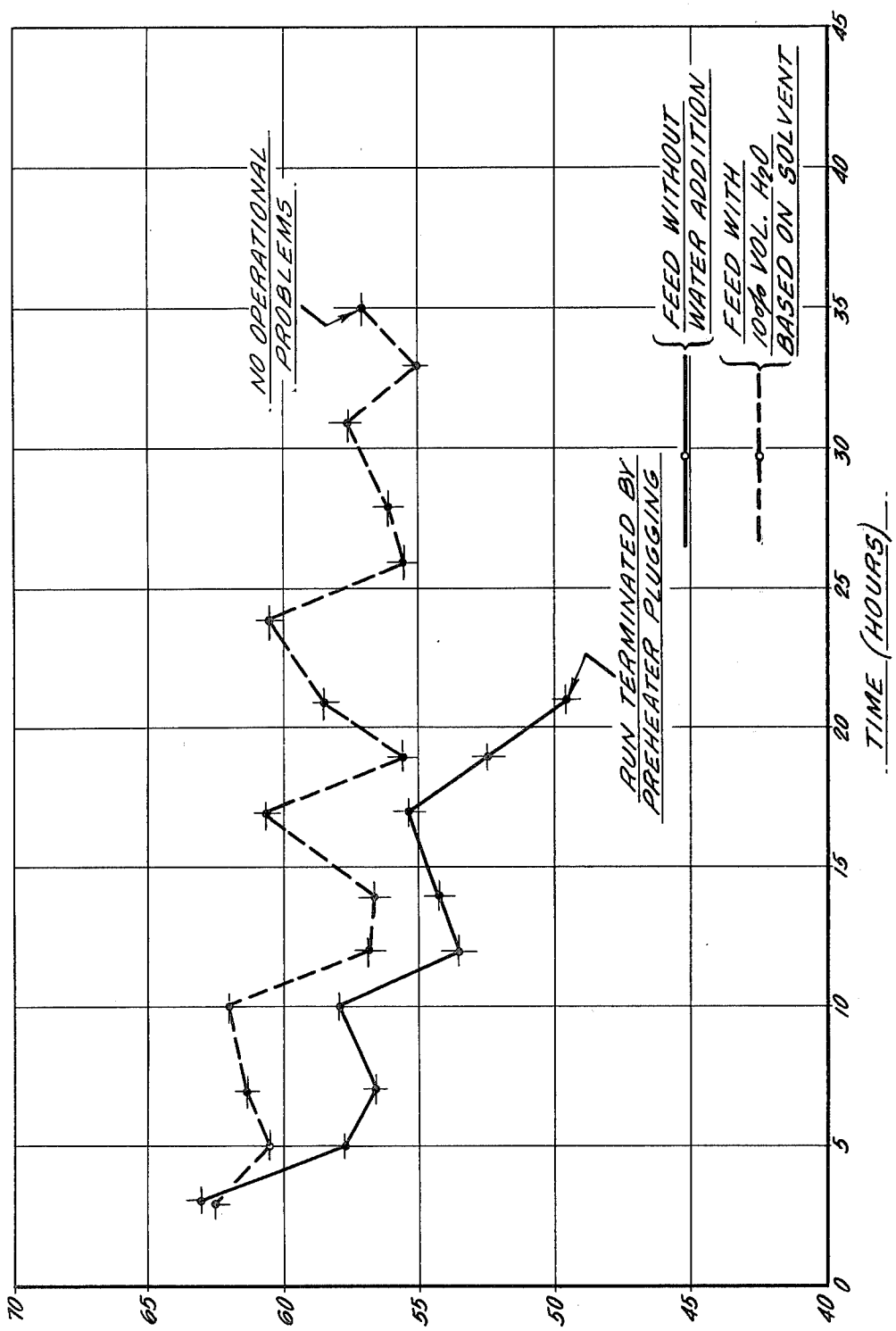
FIG. 1 is a graph showing the effect of water concentration on catalyst life.

The nitriles subject to the process of the invention will be preferably aliphatic nitriles of formula $R_1(CN_n)$ where $R_1$ is a hydrocarbon group of from one to about eighteen carbon atoms and n is a small integer, preferably 1 or 2, alkyleneoxy nitriles of formula $A+R_2-O-R_2+_mCN$ where $R_2$ is an aliphatic hydrocarbon group containing from one to about eighteen carbon atoms, A is hydrogen or a nitrile group and m is a small integer being preferably one, two, or three, and alkylene amino nitriles of formula $A+R_2-NR_3-R_2+_mCN$ where $R_3$ is hydrogen or a lower alkyl group and $R_2$, A, and m are as defined above. Examples of useful nitriles will include.

$CH_3CN$
$C_4H_9CN$
$C_{12}H_{25}CN$
$NC-(CH_2)_6-CN$
$NC-(CH_2)_{18}-CN$
$CH_3CH_2CH_2-O-CH_2CH_2-CN$
$NC-CH_2CH_2CH_2-O-CH_2CH_2-O-CH_2CH_2CH_2-CN$
$NCCH_2CH_2OCH_2CH_2CH_2OCH_2CH_2CN$
$NCCH_2CH_2OCH_2CH(CH_3)OCH_2CH_2CN$
$NCCH_2CH_2O(CH_2)_4OCH_2CH_2CN$
$NCCH_2CH_2OCH_2CH_2CH(CH_3)OCH_2CH_2CN$
$[NCCH_2CH_2OCH(CH_3)-]_2$
$(CH_3)_2C(OCH_2CH_2CN)CH_2OCH_2CH_2CN$
$NCCH_2CH_2O(CH_2)_3CH(CH_3)OCH_2CH_2CN$
$NCCH_2CH_2O(CH_2)_5OCH_2CH_2CN$
$NCCH_2CH_2O(CH_2)_6OCH_2CH_2CN$
$NCCH_2CH_2O(CH_2)_{10}OCH_2CH_2CN$
$CH_3CH_2CH_2-NH-CH_2CH_2CN$

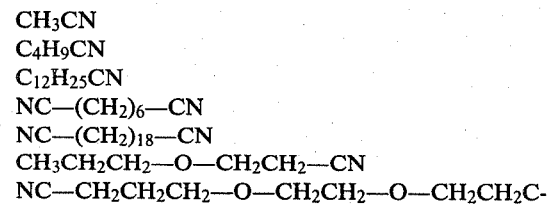

$NC-CH_2CH_2-NH-CH_2CH_2-NH_2-CH_2CH_2-CN$

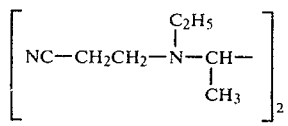

NC—CH₂CH₂NH(CH₂)₁₂NHCH₂CH₂—CN

A preferred group of nitriles used in the process will be the alkyl nitriles, alkylene dinitriles, and alkyleneoxynitriles and these will preferably contain up to about eighteen carbon atoms in the molecule. Most preferably the nitriles used will be dinitriles of the above groups.

In carrying out the process of the invention in a batch system a mixture of the solvent, nitrile, ammonia, water and catalyst is heated to a reaction temperature of from about 50° C. to about 200° C., preferably about 85° C. to about 120° C. and hydrogen introduced, with stirring, to a hydrogen pressure of from about 500 to about 3000 psig. The reaction is allowed to proceed until hydrogen uptake ceases or until aliquot samples show that all of the nitrile has been converted. Then, the reactor is cooled and vented and the contents are removed and filtered to recover the catalyst. The filtrate is distilled to recover solvent and the product is distilled under reduced pressure. A continuous operation may also be employed in which case a charge tank containing the dinitrile, solvent, ammonia and water is held under nitrogen pressure (about 200 psig) and pumped to a preheater pressured by hydrogen to about 1500 psig with the reactants exiting the preheater at about 120° C. and entering the catalyst containing reactor at about 80° C. The effluent from the reactor will be at about 130° C. and will be vented to the atmosphere to remove vaporous hydrogen and ammonia with the liquid going to a distillation recovery system for the product.

The solvent used will be an ether or a polyether (di- or tri-preferred) preferably with 4 to 6 carbon atoms and a carbon:oxygen ratio of from 2:1 to 5:1 such as dioxane, tetrahydrofuran, ethylene glycol dimethyl ether and diethyleneglycol dimethyl ether. Cyclic ethers such as dioxane and tetrahydrofuran are most preferred.

The yield of primary amines produced in the process declines as the concentration of nitrile in the solvent is increased. In general, satisfactory results are obtained with up to about 25% nitrile by weight based on solvent. Lower concentrations are preferred, but practical considerations will normally dictate about 5% as the lower limit.

The catalyst used will be a conventional cobalt ruthenium hydrogenation catalyst. The catalyst may be supported on a support such as alumina, silica, kieselguhr, silica-alumina and the like. Preferably, the supported catalyst will be pre-reduced with hydrogen and will contain 75–95% metal. The amount of catalyst used is not critical, but will usually be from 1 to about 20 wt. percent of the nitrile in a batch system.

The amount of ammonia in the reaction mass will be at least two moles of ammonia per cyano group and will usually be from about 10% to about 30% by volume of the solvent. The ammonia is believed to be helpful in supressing the formation of unwanted secondary and tertiary amine by-products.

The presence of a specific amount of water in the reaction mass is critical to the operation of the invention. In general, polymeric products result when hydrogenation of a nitrile is carried out in an aqueous system containing ammonia. However, by controlling the amount of water to from about 5% to about 15% by volume of the solvent used, the product is the desired primary amine in high yield and significantly high catalyst life is obtained.

In order to further illustrate the invention the following examples are given.

EXAMPLE 1

A continuous hydrogenation of 3,3'-(ethylenedioxy)-dipropionitrile (NC—C₂H₄—O—C₂H₄—O—C₂H₄—CN) is carried out by charging 142.8 parts by weight of the dinitrile, 567.8 parts of tetrahydrofuran, 59.5 parts of ammonia, and 64 parts of water to a holding tank pressured with nitrogen to 200 psig. This solution mixture is pumped at 103 cubic centimeters per hour to a preheater together with 1.4 liters per minute of hydrogen to a pressure of 1500 psig (weight hourly space velocity = 0.2 parts per dinitrile per part of catalyst per hour). The effluent from the preheater is at 120° C. and is fed at 80° C. to a catalytic trickle bed reactor made of stainless steel and packed with 80 parts of a 5% ruthenium on alumina catalyst (⅛" pellets). The maximum reactor temperature is 160° C. and the effluent from the reactor is vented to the atmosphere to remove gaseous ammonia and hydrogen. The remaining liquid is distilled to obtain the diamine product (H₂N—C₃H₆—O—C₂H₄—O—C₃H₆—NH₂).

As can be seen from FIG. 1, where a similar run without water is shown, the yield of product dropped off quickly and also caused operational problems after 20 hours of operation when no water was present in the system. On the other hand, when 10% by volume of water based on the solvent was present, the yield dropped off much more slowly and the process was still operating satisfactorily after thirty-five hours.

EXAMPLE 2

Using the general procedure of Example 1, but using a cobalt catalyst, hexamethylene-1,6-dinitrile is similarly hydrogenated to octamethylene diamine in good yield without operational problems.

EXAMPLE 3

Figure 2:
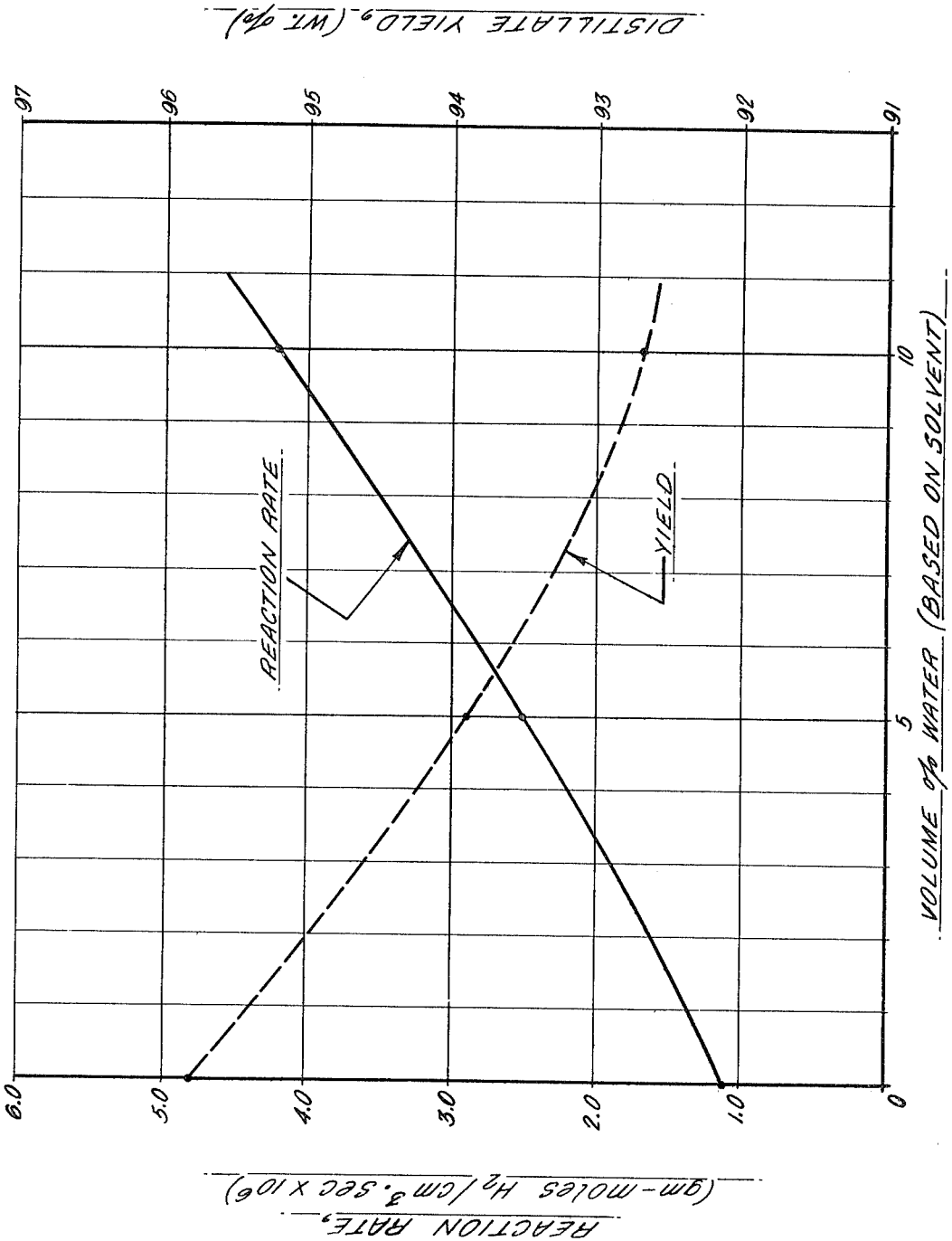
FIG. 2 is a graph showing the effect of water concentration on reaction rate and yield.

A batch reaction carried out with 3,3'-(ethylenedioxypropionitrile carried out at 135° C., 1500 psig, at a catalyst loading of 9.89 × 10⁻⁴ g. Ru/cm³ and at a rate of agitation of 800 rpm gives the results shown in FIG. 2.

As can be seen the reaction rate is significantly higher at a water concentration of from about 5% and higher, although the yield drops off with increased water in the reaction mass. Thus, a trade-off is necessary to obtain suitable yield at the higher rates and, as seen from the figure, a yield of over 92% is achievable even at the upper range of water concentration.

The invention claimed is:

1. In the process of hydrogenating aliphatic nitriles, alkyleneoxynitriles and alkylene amino nitriles to primary amines whereby the nitrile is hydrogenated in a solvent system containing added ammonia using a cobalt or ruthenium catalyst, the improvement of employing an ether as solvent and carrying out the hydrogenation in the presence of water in an amount of from about 5% to about 15% by volume of the ether solvent whereby high selectivity to primary amine products is obtained at a significantly high reaction rate.

2. The process of claim 1 where the nitriles are aliphatic nitriles of structure $R_1$—$(CN)_n$ where $R_1$ is a hydrocarbon group of one to about eighteen carbon atoms and n is 1 or 2.

3. The process of claim 1 where the nitriles are alkylenoxynitriles of formula A—$(R_2$—O—$R_2)_m$CN where A is hydrogen or nitrile, $R_2$ is an aliphatic hydrocarbon containing from one to eighteen carbon atoms, and m is a 1, 2, or 3.

4. A process for hydrogenating aliphatic nitriles of formula $R_1$—$(CN)_n$, A—$(R_2$—O—$R_2)_m$CN, or A—$(R_2NR_3$—$R_2)_m$CN where $R_1$ and $R_2$ are hydrocarbon groups of from one to about eighteen carbon atoms, $R_3$ is hydrogen or lower alkyl, A is hydrogen or nitrile, n is an integer of 1 or 2, and m is an integer of 1, 2, or 3 which comprises reacting said nitrile with hydrogen in the presence of a cobalt or ruthenium catalyst at a temperature of from about 50° C. to about 200° C. at a hydrogen pressure of from about 500 to about 3000 psig in a cyclic ether solvent containing (a) from about 5% to about 25% by weight of nitrile on the weight of said solvent, (b) from about 10% to about 30% by volume of said solvent of ammonia, and (c) from about 5% to about 15% by weight of said solvent of water, whereby high selectivity to primary amine products is obtained at a significantly high reaction rate.

5. The process of claim 4 wherein the nitrile is an aliphatic dinitrile.

6. The process of claim 5 wherein the solvent is tetrahydrofuran.

7. The process of claim 4 wherein the nitrile is an alkyleneoxydinitrile.

8. The process of claim 7 wherein the dinitrile is 3,3'-(ethylenedioxy)-di-propionitrile.

9. The process of claim 8 where the solvent is tetrahydrofuran.

10. The process of claim 4 where the nitriles are alkylene amino nitriles.

* * * * *